US008513174B2

(12) United States Patent
Araki et al.

(10) Patent No.: US 8,513,174 B2
(45) Date of Patent: Aug. 20, 2013

(54) CLEANSER

(75) Inventors: Hidefumi Araki, Yokohama (JP); Tomohiko Kimura, Yokohama (JP); Yasunari Nakama, Yokohama (JP); Kei Watanabe, Yokohama (JP); Tadashi Okawa, Ichihara (JP); Tomohiro Iimura, Ichihara (JP)

(73) Assignees: Shiseido Company Ltd., Chuo-ku, Tokyo (JP); Dow Corning Toray Co., Ltd., Chiyoda-ku, Tokyo (JP)

( * ) Notice: Subject to any disclaimer, the term of this patent is extended or adjusted under 35 U.S.C. 154(b) by 296 days.

(21) Appl. No.: 12/866,286

(22) PCT Filed: Jan. 30, 2009

(86) PCT No.: PCT/JP2009/051571
§ 371 (c)(1),
(2), (4) Date: Aug. 5, 2010

(87) PCT Pub. No.: WO2009/099007
PCT Pub. Date: Aug. 13, 2009

(65) Prior Publication Data
US 2010/0317555 A1 Dec. 16, 2010

(30) Foreign Application Priority Data

Feb. 5, 2008 (JP) .................. 2008-025060

(51) Int. Cl.
*C11D 1/02* (2006.01)
*C11D 3/16* (2006.01)
*C11D 3/37* (2006.01)
(52) U.S. Cl.
USPC ........... 510/122; 510/127; 510/130; 510/136; 510/137; 510/138; 510/466
(58) Field of Classification Search
USPC ................. 510/122, 127, 130, 136, 137, 138, 510/466
See application file for complete search history.

(56) References Cited

U.S. PATENT DOCUMENTS

| 6,184,407 B1 | 2/2001 | Yoshiake et al. |
| 6,290,942 B1 | 9/2001 | Nakazato et al. |
| 2010/0190871 A1 | 7/2010 | Araki et al. |

FOREIGN PATENT DOCUMENTS

| EP | 0685250 A1 | 12/1995 |
| EP | 1031592 | 8/2000 |
| EP | 2180028 | 4/2010 |
| JP | 8-157335 | 6/1996 |
| JP | 11-335563 | 12/1999 |
| JP | 2000-72784 | 3/2000 |
| JP | 2000-239390 | 9/2000 |
| JP | 2001-213885 | 8/2001 |
| JP | 2002-255752 | 9/2002 |
| JP | 2003-41290 | 2/2003 |
| JP | 2008-266285 | 11/2008 |
| WO | 95/23579 | 9/1995 |
| WO | 2009/022621 | 2/2009 |
| WO | 2009/025146 | 2/2009 |

OTHER PUBLICATIONS

Supplementary European Search Report dated Oct. 7, 2011; Applicant—Shiseido Company, Ltd., et al. Application No. 09708011.3-1221/2251403 PCT/JP2009051571, four pages.
Japanese Abstract for Publication No. 2001-213885 Published Aug. 7, 2001, 14 pages.
Japanese Abstract for Publication No. 2008-266285 Published Nov. 6, 2008, 40 pages.
Japanese Abstract for Publication No. 2002-255752 Published Sep. 11, 2002, 16 pages.
Japanese Abstract for Publication No. 2003-41290 Published Feb. 13, 2003, 13 pages.
International Search Report for corresponding PCT/JP2009/051579 mailed Apr. 28, 2009, three pages.
Kazuki Kageshima et al. "Application of carboxyl-modified silicone as surfacant in emulsification," Fragrance Journal extra edition 19 (2005), pp. 125-130 and partial English translation, eight pages.
Kazuki Kageshima et al. "Application of carboxyl-modified silicone as surfactant in cosmetic field," Journal of SCCJ vol. 34, No. 4 (2003) pp. 309-314 and partial English translation, eight pages.
International Preliminary Report on Patentability for corresponding PCT/JP2009/051571 mailed Sep. 16, 2010, eight pages.

*Primary Examiner* — Gregory Delcotto
(74) *Attorney, Agent, or Firm* — Rankin, Hill & Clark LLP

(57) ABSTRACT

The present invention provides a cleanser which is excellent in both of the foaming property and the cleansing capability. The cleanser comprises an organosiloxane derivative salt represented by the following formula (1) or (3) and one or more anionic surfactants selected from a group consisting of carboxylate salt with an alkyl group having 10 to 20 carbon atoms, sulfate salt with an alkyl group having 10 to 20 carbon atoms, sulfonate salt with an alkyl group having 10 to 20 carbon atoms, and phosphate salt with an alkyl group having 10 to 20 carbon atoms.

(1)

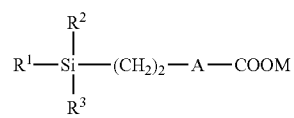

(3)

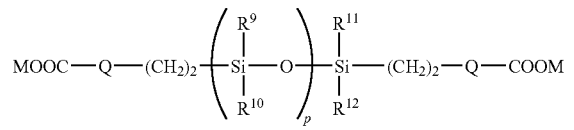

8 Claims, No Drawings

CLEANSER

RELATED APPLICATIONS

This application claims the priority of Japanese Patent Application No. 2008-025060 filed on Feb. 5, 2008, which is incorporated herein by reference.

FIELD OF THE INVENTION

The present invention relates to a cleanser containing a specifically structured organosiloxane derivative, in particular, relates to a cleanser with both a good foaming property and a good cleansing capability.

BACKGROUND OF THE INVENTION

Heretofore, organo(poly)siloxanes having various organic groups introduced in a portion of their structures have been developed by use of properties specific to dimethylpolysiloxane typified by silicone oil. Such organo(poly)siloxanes have low surface tension and a low refractive index and further have properties in combination, such as low susceptibility to friction, heat resistance, cold resistance, antistatic properties, water repellency, mold releasability, anti-foaming properties, and chemical resistance. Therefore, they are used in various fields. There exist organo(poly)siloxanes modified at various functional groups or at structural positions for introduction thereof, according to the usage.

Various compounds have been developed and studied so far, for example, as organo(poly)siloxane derivatives containing a carboxyl group, which is a hydrophilic organic group. As typical examples, organosiloxane derivatives having a carboxyl group introduced in the side chain of a linear polysiloxane structure are widely known. In recent years, siloxane dendrimers containing a carboxyl structure have also been reported as one example of such compounds (see e.g., Patent Literatures 1 to 3). Furthermore, it has also been reported that a compound obtained by neutralizing carboxyl-modified silicone with triethanolamine has an emulsification capacity (see e.g., Non-Patent Literatures 1 and 2).

On the other hand, in the conventional skin cleansers or hair cleansers, an anionic or non-ionic surfactant is generally incorporated as a major component of the cleansing agents. In contrast, in most makeup products, hair waxes, and so on, silicone compounds are incorporated for the purpose of providing long-lasting finish, water resistance, and smoothness during and after application. When a normal surfactant was used as a cleansing agent, there have been problems that these silicone compounds could not be washed off sufficiently. In this context, the use of a silicone oil or a silicone surfactant could improve the cleansing effect. However, the anti-foaming effect of the silicones has caused a problem that the foaming was very bad.

Patent Literature 1: Japanese Unexamined Patent Publication 2000-072784

Patent Literature 2: Japanese Unexamined Patent Publication 2000-239390

Patent Literature 3: Japanese Unexamined Patent Publication 2001-213885

Non-patent Literature 1: Kazuki KAGESHIMA and Toshiyuki SHIMIZU, "Application of carboxyl-modified silicone as surfactant in emulsification," Fragrance Journal extra edition 19 (2005): 125-130

Non-patent Literature 2: Kazuki KAGESHIMA, Harumi SAKAMOTO, and Toshiyuki SHIMIZU, "Application of carboxyl-modified silicone as surfactant in cosmetic field," Journal of SCCJ Vol. 34 No. 4 (2003): 309-314

DISCLOSURE OF THE INVENTION

Problem to be Solved by the Invention

The present invention has been conducted in view of the problems of the prior art, and an object of the present invention is to provide a cleanser which is excellent in both of the foaming property and the cleansing capability.

Means to Solve the Problem

To solve the problems of the prior art, the present inventors have studied diligently and found that both of an excellent cleansing effect and a significantly improved foaming property can be achieved by incorporating a specifically structured organosiloxane derivative salt with a carboxyl group and anionic surfactants such as a fatty acid soap into a cleanser, thus leading to completion of the present invention.

The cleanser according to the present invention is characterized by comprising an organosiloxane derivative salt represented by the following formula (1) or (3) and one or more of carboxylate salt with an alkyl group having 10 to 20 carbon atoms, sulfate salt with an alkyl group having 10 to 20 carbon atoms, sulfonate salt with an alkyl group having 10 to 20 carbon atoms, or phosphate salt with an alkyl group having 10 to 20 carbon atoms.

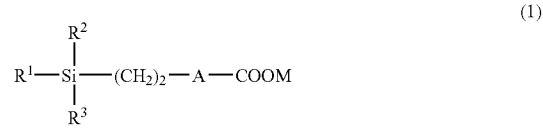

(1)

In the formula (1), at least one of $R^1$ to $R^3$ is a functional group represented by $-O-Si(R^4)_3$ in which $R^4$ is an alkyl group having 1 to 6 carbon atoms or a phenyl group, or a functional group represented by $-O-Si(R^5)_2-X^1$ in which $R^5$ is an alkyl group having 1 to 6 carbon atoms or a phenyl group, and $X^1$ is a functional group represented by the following formula (2) when i=1; and the remaining $R^1$ to $R^3$ may be the same or different and each may be a substituted or unsubstituted monovalent hydrocarbon group; M is a metal atom or an organic cation; A is a linear or branched alkylene group represented by $C_qH_{2q}$ in which q is any integer of 0 to 20; and the organosiloxane derivative represented by the formula (1) contains a total of 2 to 100 silicon atoms (Si) on average per molecule.

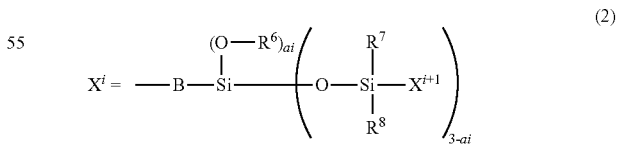

(2)

In the formula (2), $R^6$ is a hydrogen atom, an alkyl group having 1 to 6 carbon atoms, or a phenyl group; $R^7$ and $R^8$ are respectively an alkyl group having 1 to 6 carbon atoms or a phenyl group; B is a linear or branched alkylene group represented by $C_rH_{2r}$ which may be partially branched in which r is any integer of 2 to 20; and i specifies the generation of a silylalkyl group represented by $X^i$ and is any integer of 1 to n when the generation number is n, wherein the generation number n is any integer of 1 to 10; ai is any integer of 0 to 2 when i is 1, and is an integer smaller than 3 when i is 2 or larger; and $X^{i+1}$ is the silylalkyl group when i is smaller than n, and is a methyl group when i=n.

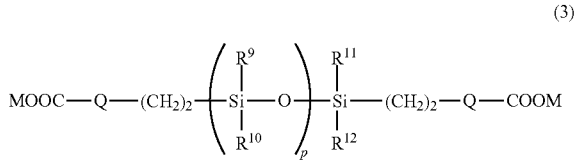

In the formula (3), $R^9$ to $R^{12}$ may be the same or different and are respectively a substituted or unsubstituted monovalent hydrocarbon group; M is a metal atom or an organic cation; Q is a linear or branched alkylene group represented by $C_qH_{2q}$ in which q is any integer of 0 to 20; and p is any number of 0 to 100.

Moreover, in the cleanser, it is preferred that the organosiloxane derivative should be represented by the formula (1), wherein $R^1$ and $R^2$ are respectively a functional group represented by —O—Si$(R^4)_3$ in which $R^4$ is an alkyl group having 1 to 6 carbon atoms; $R^3$ is a monovalent hydrocarbon group having 1 to 10 carbon atoms; and q is any integer of 6 to 20.

Moreover, in the cleanser, it is preferred that the organosiloxane derivative should be represented by the formula (1), wherein at least one or more of $R^1$ to $R^3$ are respectively a functional group represented by the following formula (4) or (5), and the remaining $R^1$ to $R^3$ may be the same or different and are respectively a substituted or unsubstituted monovalent hydrocarbon group.

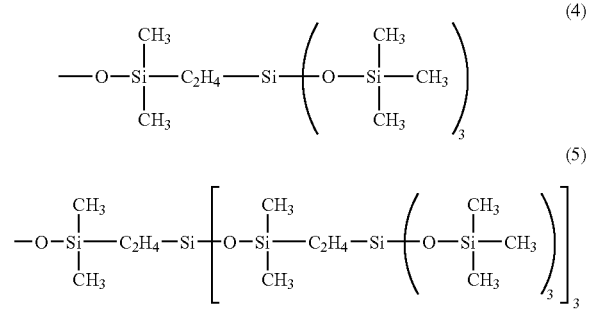

Moreover, in the cleanser, it is preferred that the organosiloxane derivative should be represented by the formula (3), wherein $R^9$ to $R^{12}$ are respectively a group selected from the group consisting of substituted or unsubstituted alkyl groups having 1 to 20 carbon atoms, aryl groups, and aralkyl groups; q is any integer of 6 to 20; and p is any number of 1 to 20.

Moreover, in the cleanser, it is preferred that the anionic surfactant should be one or more of fatty acid soap, acylmethyltaurine salt, or alkyl ether carboxylic acid salt.

Effect of the Invention

According to the present invention, both of an excellent cleansing effect and a significantly improved foaming property can be achieved by incorporating a specifically structured organosiloxane derivative salt with a carboxyl group and anionic surfactants such as a fatty acid soap into a cleanser.

BEST MODE FOR CARRYING OUT THE INVENTION

Hereinafter, the preferred embodiments of the present invention will be described.

The cleanser according to the present invention is characterized by comprising a specifically structured organosiloxane derivative salt with a carboxyl group and anionic surfactants such as a fatty acid soap.

Organosiloxane Derivative

The organosiloxane derivative used in the present invention is a compound represented by the formula (1) or (3).

First, the organosiloxane derivative represented by the following formula (1) will be described.

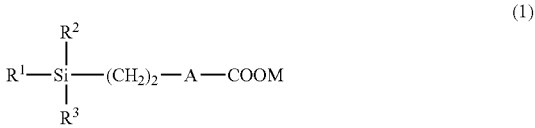

The organosiloxane derivative represented by the formula (1) is an organosiloxane derivative modified with an alkylcarboxyl group and is characterized by containing a total of 2 to 100 silicon atoms on average per molecule.

In the formula (1), at least one of $R^1$ to $R^3$ is a functional group represented by —O—Si$(R^4)_3$ in which $R^4$ is an alkyl group having 1 to 6 carbon atoms or a phenyl group, or a functional group represented by —O—Si$(R^5)_2$—$X^1$ in which $R^5$ is an alkyl group having 1 to 6 carbon atoms or a phenyl group, and $X^1$ is a functional group represented by the following formula (2) when i=1. In this context, all of $R^1$ to $R^3$ may respectively be any of the functional groups. Alternatively, when at least one of $R^1$ to $R^3$ is any of the functional groups, the remaining $R^1$ to $R^3$ may be the same or different and each may be a substituted or unsubstituted monovalent hydrocarbon group.

In the functional group represented by —O—Si$(R^4)_3$, $R^4$ is an alkyl group having 1 to 6 carbon atoms or a phenyl group. Examples of the alkyl group having 1 to 6 carbon atoms include linear, branched, or cyclic alkyl groups such as methyl, ethyl, n-propyl, i-propyl, n-butyl, i-butyl, s-butyl, t-butyl, pentyl, neopentyl, cyclopentyl, and hexyl. Examples of the functional group represented by —O—Si$(R^4)_3$ include —O—Si$(CH_3)_3$, —O—Si$(CH_3)_2(C_2H_5)$, —O—Si$(CH_3)_2(C_3H_7)$, —O—Si$(CH_3)_2(C_4H_9)$, —O—Si$(CH_3)_2(C_5H_{11})$, —O—Si$(CH_3)_2(C_6H_{13})$, —O—Si$(CH_3)_2(C_6H_5)$. In this context, the functional group is preferably a trialkylsiloxy group, most preferably a trimethylsiloxy group.

Moreover, the functional group represented by —O—Si$(R^5)_2$—$X^1$ is an organosiloxy group having a dendrimer structure. $R^5$ is an alkyl group having 1 to 6 carbon atoms or a phenyl group. Moreover, $X^1$ is a functional group represented by the following formula (2) when i=1.

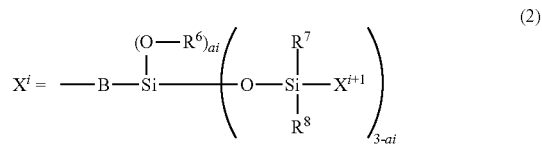

In the formula (2), $R^6$ is a hydrogen atom, an alkyl group having 1 to 6 carbon atoms, or a phenyl group, and $R^7$ and $R^8$ are respectively an alkyl group having 1 to 6 carbon atoms or a phenyl group. $R^6$ to $R^8$ are respectively preferably an alkyl group having 1 to 6 carbon atoms, particularly preferably a methyl group. Moreover, B is a linear or branched alkylene group represented by $C_rH_{2r}$ which may be partially branched, and r is any integer of 2 to 20. Examples of the alkylene group having 2 to 20 carbon atoms, represented by B include: linear alkylene groups such as ethylene, propylene, butylene, and hexylene groups; and branched alkylene groups such as methylmethylene, methylethylene, 1-methylpentylene, and 1,4-dimethylbutylene groups. Among them, an ethylene or hexylene group is preferable.

In the formula (2), i specifies the generation of a silylalkyl group represented by $X^i$ and is any integer in the range of 1 to n when the generation number, i.e., the number of repetitions of the silylalkyl group, is n. The generation number n is any integer of 1 to 10. $X^{i+1}$ is the silylalkyl group when i is smaller than n, and is a methyl group ($-CH_3$) when i=n. ai is any integer of 0 to 2 when i=1, and is a number smaller than 3 when i is 2 or larger. ai is preferably 1 or smaller, particularly preferably 0.

Specifically, when the generation n of the dendrimer structure is 1, the silylalkyl group of the formula (2) is represented by the following formula.

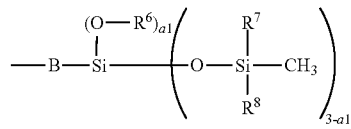

When the generation n of the dendrimer structure is 2, the silylalkyl group of the formula (2) is represented by the following formula.

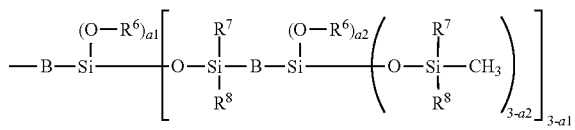

When the generation n of the dendrimer structure is 3, the silylalkyl group of the formula (2) is represented by the following formula.

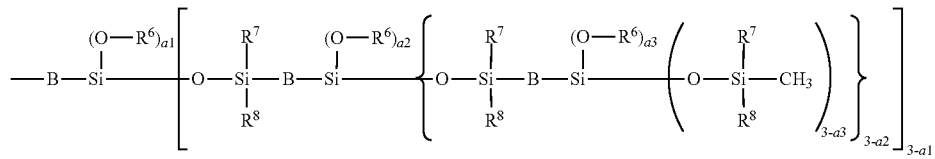

Particularly, it is preferred that examples of the functional group represented by $-O-Si(R^5)_2-X^1$ include a functional group represented by the following formula (4) wherein the generation number n of the silylalkyl group is 1, a functional group represented by the following formula (5) wherein the generation number n of the silylalkyl group is 2, and a functional group represented by the following formula (6) wherein the generation number n of the silylalkyl group is 3.

(4)

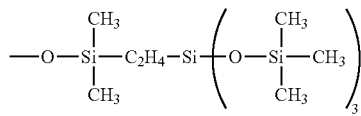

(5)

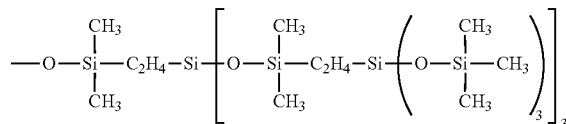

(6)

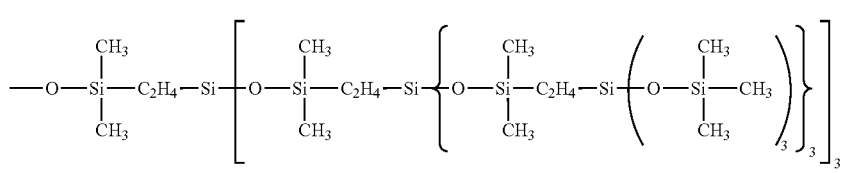

Moreover, in the formula (1), as long as at least one of $R^1$ to $R^3$ is the functional group represented by —O—Si$(R^4)_3$ or the functional group represented by —O—Si$(R^5)_2$—$X^1$, the remaining $R^1$ to $R^3$ may be the same or different and each may be a substituted or unsubstituted monovalent hydrocarbon group. Examples of the unsubstituted monovalent hydrocarbon group as $R^1$ to $R^3$ include: linear, branched, or cyclic alkyl groups such as methyl, ethyl, n-propyl, i-propyl, n-butyl, i-butyl, s-butyl, pentyl, neopentyl, cyclopentyl, and hexyl; aryl groups such as phenyl, tolyl, and xylyl groups; and aralkyl groups. Examples of the substituted monovalent hydrocarbon group as $R^1$ to $R^3$ include: perfluoroalkyl groups such as 3,3,3-trifluoropropyl and 3,3,4,4,4-pentafluorobutyl groups; aminoalkyl groups such as 3-aminopropyl and 3-(aminoethyl)aminopropyl groups; and amidoalkyl groups such as acetylaminoalkyl groups. Moreover, the hydrocarbon group as $R^1$ to $R^3$ may be partially substituted by a hydroxyl, alkoxy, polyether, or perfluoropolyether group. Examples of the alkoxy group include methoxy, ethoxy, and propoxy groups.

In the formula (1), when one or two of $R^1$ to $R^3$ are respectively the functional group represented by —O—Si$(R^4)_3$ or the functional group represented by —O—Si$(R^5)_2$—$X^1$, the remaining $R^1$ to $R^3$ are respectively preferably a linear or branched alkyl group having 1 to 6 carbon atoms, particularly preferably a methyl or ethyl group. Particularly, in the formula (1), it is preferred that all or two of $R^1$ to $R^3$ should respectively be the functional group represented by —O—Si$(R^4)_3$ or the functional group represented by —O—Si$(R^5)_2$—$X^1$, and the remaining $R^1$ to $R^3$ should be a methyl or ethyl group.

Moreover, M is a metal atom or an organic cation. Examples of the metal atom include monovalent alkali metals, divalent alkali metals, and di- or higher valent metal atoms. Examples of the monovalent alkali metals include Li, Na, and K. Examples of the divalent alkali metals include Mg, Ca, and Ba. Other examples of the metal atom include Mn, Fe, Co, Al, Ni, Cu, V, Mo, Nb, Zn, and Ti. Moreover, examples of the organic cation include ammonium, aminomethyl propanol (AMP)-neutralized, triethanolammonium, diethanolammonium, monoethanolammonium, triisopropanolammonium, L arginine-neutralized, and L lysine-neutralized ions. M is particularly preferably a monovalent alkali metal or may be a mixture thereof.

A is a linear or branched alkylene group represented by $C_qH_{2q}$, and q is any integer of 0 to 20. In this context, when q=0, the organosiloxane derivative represented by the formula (1) is a compound represented by the following formula (1-A), wherein the carboxyl-modified group is bound with silicon via an ethylene group. In the present invention, q is preferably any integer of 2 to 15, more preferably any integer of 6 to 12. On the other hand, if q exceeds the upper limit, the foaming property may be poor.

$$R^1R^2R^3Si—(CH_2)_2—COOM \quad (1\text{-A})$$

Moreover, the organosiloxane derivative represented by the formula (1) is characterized by containing a total of 2 to 100 silicon atoms on average per molecule. The organosiloxane derivative represented by the formula (1) contains preferably a total of 3 to 30 silicon atoms on average. On the other hand, if the total number of the silicon atoms per molecule exceeds 100, the foaming property may be poor.

The organosiloxane derivative represented by the formula (1) that can be used preferably is more specifically an organosiloxane derivative wherein $R^1$ and $R^2$ are respectively a functional group represented by —O—Si$(R^4)_3$ in which $R^4$ is an alkyl group having 1 to 6 carbon atoms; $R^3$ is a linear or branched alkyl group having 1 to 6 carbon atoms; and q is any integer of 6 to 12.

The organosiloxane derivative represented by the formula (1) is obtained by causing addition reaction between polysiloxane containing a silicon-bound hydrogen atom, represented by $R^1R^2R^3SiH$ and a trimethylsilyl carboxylate derivative having a vinyl end, represented by CH=$CH_2$—A—COOSiMe$_3$ in the presence of a platinum-based catalyst, adding, to the reaction product, at least 1 mol of a monohydric alcohol (e.g., methanol) per mol of the trimethylsilyl group as a protective group, heating the mixture to deprotect the protective group by alcoholysis, and further neutralizing the mixture with a compound containing a proper metal ion ($M^{n+}$) or a basic organic compound. In this context, $R^1$, $R^2$, $R^3$, A, and M are as defined above. Example of the neutralization step includes a step of neutralizing a carboxyl group (—COOH) by adding an aqueous solution such as sodium hydroxide (NaOH), potassium hydroxide (KOH), triethanolamine, arginine, or aminomethyl propanol (AMP).

On the other hand, when the neutralization step using the metal ion containing compound or the basic organic compound is not performed after the deprotection, an organosiloxane derivative having a terminal carboxyl group, represented by the following formula (1'), can be obtained.

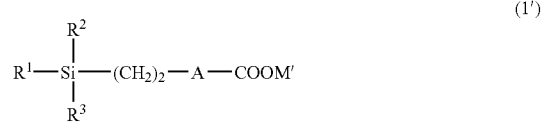

(1')

In the formula (1'), $R^1$ to $R^3$ and A are as defined above, and M' is a hydrogen atom. The organosiloxane derivative represented by the formula (1') contains a total of 2 to 150 silicon atoms (Si) on average per molecule.

In the present invention, the organosiloxane derivative represented by the formula (1) can be obtained easily by mixing the organosiloxane derivative having a terminal carboxyl group, represented by the formula (1'), with a solution containing a metal ion or an organic cation to cause the cation exchange reaction of the terminal carboxyl group. For this reason, the organosiloxane derivative represented by the formula (1') and the metal ion containing compound or the basic organic compound may be individually incorporated into the cleanser. Examples of the metal ion containing compound or the basic organic compound include the compounds as defined above. The amount of the metal ion containing compound or the basic organic compound used with respect to the organosiloxane derivative having a terminal carboxyl group, represented by the formula (1'), is preferably in the range of 6:1 to 2:1 in the mass ratio of the organosiloxane derivative: the metal ion containing compound or the basic organic compound. However the amount is not limited thereto in particular.

Moreover, the method for producing the organosiloxane derivative represented by the formula (1) is described in detail in Japanese Unexamined Patent Publication Nos. 2000-072784, 2000-239390, and 2001-213885. The organosiloxane derivative of the present invention represented by the formula (1) can be produced easily, particularly by a production method comprising the following steps (1) to (4).

Step (1):

The step of causing addition reaction between organosilane having a dimethylsiloxy group, represented by

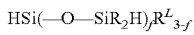

(wherein R is an alkyl group having 1 to 6 carbon atoms or a phenyl group; $R^L$ may be the same or different and is a substituted or unsubstituted monovalent hydrocarbon group; and f is any integer of 1 to 3) and a trimethylsilyl carboxylate derivative having a vinyl end, represented by $CH=CH_2-A-COOSiMe_3$ (wherein A is as defined above) in the presence of a platinum-based transition metal catalyst to obtain an intermediate (1-1) of the following formula:

$$Si(-O-SiR_2H)_f R^L_{3-f}-(CH_2)_2-A-COOSiMe_3 \qquad (1\text{-}1)$$

Step (2):

The step of causing addition reaction between organosilane having an alkenyl group, represented by

(wherein $R^B$ is a linear or branched alkenyl group represented by $C_rH_{2r}$; r is any integer of 2 to 20; and $R^6, R^7, R^8, X^{i+1}$, and ai are as defined above) and the intermediate (1-1) in the presence of a platinum-based catalyst to obtain an intermediate (1-2) of the following formula:

$$Si\{-O-SiR_2-B-Si(O-R^6)_{ai}(OSiR^7R^8-X^{i+1})_{3-ai}\}_f R^L_{3-f}-(CH_2)_2-A-COOSiMe_3 \qquad (1\text{-}2)$$

Step (3):

The step of adding, to the intermediate (1-2), at least 1 mol or more of a monohydric alcohol (e.g., methanol), water, or a mixture thereof per mol of the trimethylsilyl group as a protective group, and heating the mixture to deprotect the protective group by alcoholysis.

Step (4):

The step of neutralizing the reaction product in Step (3) with a compound containing a metal ion ($M^{n+}$) or a basic organic compound.

Examples of the neutralization step include a step of neutralizing a carboxyl group (—COOH) by adding an aqueous solution such as sodium hydroxide (NaOH), potassium hydroxide (KOH), triethanolamine, arginine, and aminomethyl propanol (AMP).

Subsequently, the organosiloxane derivative represented by the following formula (3) will be described.

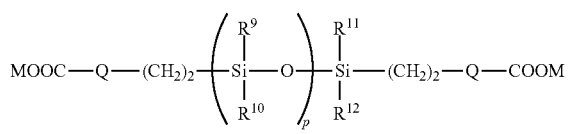

(3)

The organosiloxane derivative represented by the formula (3) is an organosiloxane derivative modified, at both ends of the molecular chain, with an alkylcarboxyl group.

In the formula (3), $R^9$ to $R^{12}$ may be the same or different and are selected from substituted or unsubstituted monovalent hydrocarbon groups. Examples of the unsubstituted monovalent hydrocarbon group represented by $R^9$ to $R^{12}$ include: linear or branched alkyl groups such as methyl, ethyl, propyl, butyl, pentyl, hexyl, heptyl, octyl, decyl, and dodecyl groups; linear or branched alkenyl groups such as allyl and hexenyl groups; cycloalkyl groups such as cyclopentyl and cyclohexyl groups; aryl groups such as phenyl, tolyl, and naphthyl groups; and aralkyl groups such as benzyl, phenylethyl, phenylpropyl, naphthylmethyl, and naphthylethyl groups. Examples of the substituted monovalent hydrocarbon group represented by $R^9$ to $R^{12}$ include groups in which hydrogen atoms bound with the carbon atoms of the hydrocarbon groups described above are partially substituted by an organic group such as a hydroxyl group, a halogen atom, an epoxy group, an amino group, a methacryl group, a mercapto group, an alkoxy group, a polyether group, or a perfluoropolyether group and specifically include: perfluoroalkyl groups such as 3,3,3-trifluoropropyl and 3,3,4,4,4-pentafluorobutyl groups; aminoalkyl groups such as 3-aminopropyl and 3-(aminoethyl)aminopropyl groups; and amidoalkyl groups such as acetylaminoalkyl groups. $R^9$ to $R^{12}$ are respectively preferably an alkyl group having 1 to 20 carbon atoms, an aryl group, or an aralkyl group. It is particularly preferred that 90% by mol or more of $R^9$ to $R^{12}$ in one molecule should be a methyl group and/or a phenyl group.

Moreover, M is a metal, atom or an organic cation. Examples of the metal atom include monovalent alkali metals, divalent alkali metals, and di- or higher valent metal atoms. Examples of the monovalent alkali metals include Li, Na, and K. Examples of the divalent alkali metals include Mg, Ca, and Ba. Other examples of the metal atom include Mn, Fe, Co, Al, Ni, Cu, V, Mo, Nb, Zn, and Ti. Moreover, examples of the organic cation include ammonium, aminomethyl propanol (AMP)-neutralized, triethanolammonium, diethanolammonium, monoethanolammonium, triisopropanolammonium, L arginine-neutralized, and L lysine-neutralized ions. M is particularly preferably a monovalent alkali metal or may be a mixture thereof.

Q is a linear or branched alkylene group represented by $C_qH_{2q}$, and q is any integer of 0 to 20. In this context, when q=0, the organosiloxane derivative represented by the formula (3) is a compound represented by the following formula (3-A), wherein the carboxyl-modified group is bound with silicon via an ethylene group. In the present invention, q is preferably any integer of 6 to 20, more preferably any integer of 6 to 12. On the other hand, if q exceeds the upper limit, the foaming property may be poor.

$$MOOC-(CH_2)_2-(SiR^9R^{10}-O)_p-SiR^{11}R^{12}-(CH_2)_2-COOM \qquad (3\text{-}A)$$

In the formula (3), p specifies the average degree of polymerization of di-substituted polysiloxane and is any number of 0 to 150, In the present invention, p is more preferably any number of 1 to 20, particularly preferably any number of 1 to 10. On the other hand, if p exceeds the upper limit, the foaming property may be poor.

The organosiloxane derivative represented by the formula (3) that can be used preferably is an organosiloxane derivative wherein $R^9$ to $R^{12}$ are respectively an alkyl group having 1 to 6 carbon atoms; q is any integer of 0 to 20; and p is any number of 0 to 20.

The organosiloxane derivative represented by the formula (3) is obtained by causing addition reaction between organohydrogenpolysiloxane having a silicon-bound hydrogen atom at both ends of the molecular chain, represented by

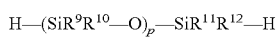

(wherein $R^9$ to $R^{12}$, p, and q are as defined above) and at least 2 mol of a trimethylsilyl carboxylate derivative having a vinyl end, represented by $CH=CH_2-Q-COOSiMe_3$ with respect to 1 mol of the organohydrogenpolysiloxane in the presence of a platinum-based catalyst, adding, to the reaction product, at least 1 mol or more of a monohydric alcohol (e.g., methanol), water, or a mixture of these compositions per mol of the trimethylsilyl group as a protective group, heating the mixture to deprotect the protective group by alcoholysis, and further neutralizing the mixture with a compound containing a proper metal ion ($M^{n+}$) or a basic organic compound. In this context, Q is as defined above. Examples of the metal ion containing compound or the basic organic compound used in the neutralization step are as defined above.

On the other hand, when the neutralization step using the metal ion containing compound or the basic organic compound is not performed after the deprotection, an organosiloxane derivative having a terminal carboxyl group, represented by the following formula (3'), can be obtained.

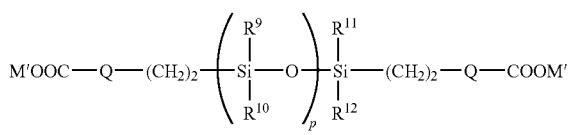

(3')

In the formula (3'), $R^9$ to $R^{12}$ and Q are as defined above; p is as defined above; and M' is a hydrogen atom.

In the present invention, the organosiloxane derivative represented by the formula (3) can be obtained easily by mixing the organosiloxane derivative having a terminal carboxyl group, represented by the formula (3'), with a solution containing a metal ion or an organic cation to cause the cation exchange reaction of the terminal carboxyl group. For this reason, the organosiloxane derivative represented by the formula (3') and the metal ion containing compound or the basic organic compound may be individually incorporated into the cleanser. Examples of the metal ion containing compound or the basic organic compound include the metal salts as defined above. The amount of the metal ion containing compound or the basic organic compound used with respect to the organosiloxane derivative having a terminal carboxyl group, represented by the formula (3'), is preferably in the range of 6:1 to 2:1 in the mass ratio of the organosiloxane derivative: the metal ion containing compound or the basic organic compound. However, the amount is not limited thereto in particular.

The platinum-based catalyst used for producing the organosiloxane derivative of the present invention represented by the formula (1) or (3) is a catalyst for hydrosilylation reaction between the silicon-bound hydrogen atom and the alkenyl group. Examples thereof include chloroplatinic acid, alcohol-modified chloroplatinic acid, olefin complexes of platinum, ketone complexes of platinum, vinylsiloxane complexes of platinum, platinum tetrachloride, fine platinum powders, solid platinum supported by an alumina or silica carrier, platinum black, olefin complexes of platinum, alkenylsiloxane complexes of platinum, carbonyl complexes of platinum, and thermoplastic organic resin (e.g., methyl methacrylate, polycarbonate, polystyrene, and silicone resins) powders containing these platinum-based catalysts. Preferably, the platinum-based catalyst is a 1,3-divinyl-1,1,3,3-tetramethyldisiloxane complex of platinum or chloroplatinic acid.

The organosiloxane derivative represented by the formula (1) or (3) can be solely incorporated in the cleanser according to the present invention.

The organosiloxane derivative represented by the formula (1') or (3') can be used in the cleanser according to the present invention by incorporating the organosiloxane derivative together with the metal ion containing compound or the basic organic compound in the cleanser. Specifically, in the present invention, the terminal carboxyl group of the organosiloxane derivative only needs to be in a state that it can become a metal salt or an organic salt (that is, the organosiloxane derivative represented by the formula (1) or (3)) in the formulation of the cleanser. Thus, the organosiloxane derivative having a terminal carboxyl group and the metal ion containing compound or the basic organic compound can be individually incorporated into the cleanser.

The amount of the organosiloxane derivative incorporated in the cleanser of the present invention is not particularly limited and is usually 0.1 to 30% by mass, preferably 1 to 10% by mass, more preferably 3 to 5% by mass, of the total amount of the composition. If the organosiloxane derivative is incorporated in too small an amount, a sufficient cleansing effect on the silicone compound may not be achieved. Moreover, if the organosiloxane derivative is incorporated in too large an amount, the foaming property may become poor.

Anionic Surfactants

The anionic surfactant used in the present invention can be selected from carboxylate salt, sulfate salt, sultanate salt, or phosphate salt, in which these compounds contain an alkyl group having 10 to 20 carbon atoms (hereinafter they are also referred to as various anionic surfactants simply). These various anionic surfactants are the salts of various acids having a saturated or unsaturated alkyl group, and the alkyl chain can be either linear or branched. Also, the various anionic surfactants can have other functional groups (such as an amino group and an ether group) or chain structures (such as a polyoxyalkylene group) in addition to the alkyl chain. In the present invention, the various acid salts can be incorporated in the cleanser in a state that the salts have been already formed, or the various acids and a basic material can be individually incorporated in the cleanser to form its salts in the formulation of the cleanser. For example, by adding an alkylcarboxylic acid and a potassium hydroxide individually to the formulation of the cleanser, alkylcarboxylic acid potassium salt is formed in a neutralization reaction within the formulation. Examples of the basic material for forming salts in the neutralization with the various acids include hydroxides of alkali metals such as potassium hydroxide and sodium hydroxide, and basic nitrogen containing compounds such as 2-amino-2-methyl-1-propanol, 2-amino-2-methyl-1,3-propanediol, triethanolamine, diethanolamine, monoethanolamine, triisopropanolamine, 2-amino-2-hydroxymethyl-1,3-propanediol, L-arginine, L-lisine, morpholine, and N-alkyltaurine salt.

Examples of the carboxylate salt with an alkyl group having 10 to 20 carbon atoms, sulfate with an alkyl group having 10 to 20 carbon atoms, sulfonate with an alkyl group having 10 to 20 carbon atoms, and phosphate with an alkyl group having 10 to 20 carbon atoms include; fatty acid (alkylcarboxylic acid) salts such as potassium laurate, sodium laurate, triethanolammonium laurate, potassium myristate, sodium myristate, triethanolammonium myristate, potassium palmitate, sodium palmitate, potassium stearate, sodium stearate, potassium isostearate, sodium isostearate, potassium behenate, sodium behenate, potassium linoleate, sodium linoleate, potassium oleate, sodium oleate, potassium arachidate, potassium 2-palmitoleate, potassium petroselinate, potassium elaidate, potassium ricinoleate, potassium linoelaidate, potassium linolenate, potassium arachidonate, and potassium 12-hydroxystearate; N-acyl amino acid salts such as sodium N-lauroyl glutamate, sodium N-myristoyl glutamate, sodium N-coconut oil fatty acid acyl glutamate, potassium N-lauroyl glutamate, potassium N-myristoyl glutamate, potassium N-coconut oil fatty acid acyl glutamate, triethanolammonium N-lauroyl glutamate, triethanolammonium N-myristoyl glutamate, triethanolammonium N-coconut oil fatty acid acyl glutamate, sodium N-lauroyl glycinate, triethanolammonium N-myristoyl glycinate, potassium N-lauroyl-β-alaninate, triethanolammonium N-lauroyl threoninate, sodium N-lauroyl sarcosinate, sodium N-lauroyl N-methyl-β-alaninate, and triethanolammonium N-lauroyl-N-methyl-β-alaninate; acyl iminodiacetic acid salts such as sodium lauroyl iminodiacetate, triethanolarmmonium lauroyl iminodiacetate, sodium coconut oil fatty acid acyl iminodiacetate, disodium lauroyl iminodiacetate, and sodium palm kernel fatty acid iminodiacetate; polyether carboxylates such as sodium polyoxyethylene lauryl ether acetate, potassium polyoxyethylene myristyl ether acetate, triethanolammonium polyoxyethylene palmityl ether acetate, sodium polyoxyethylene stearyl ether acetate, and sodium polyglyceryl lauryl ether acetate; acylated peptides such as coconut oil fatty acid silk peptide; amide ether carboxylates such as sodium polyoxyethylene laurylamido ether carboxylate, sodium polyoxyethylene myristylamido ether carboxylate, and triethanolammonium polyoxyethylene coconut oil fatty acid amide ether carboxylate; acyl lactate; alkenyl succinates; alkyl sulfates such as sodium lauryl sulfate, potassium lauryl sulfate, sodium myristyl sulfate, potassium myristyl sulfate, sodium cetyl sulfate, sodium stearyl sulfate, sodium oleyl sulfate, and triethanolammonium lauryl sulfate; alkyl ether sulfates such as sodium polyoxyethylene lauryl ether sulfate, sodium polyoxyethylene cetyl ether sulfate, sodium polyoxyethylene oleyl ether sulfate, and triethanolammonium polyoxyethylene lauryl ether sulfate; alkyl aryl ether sulfates such as sodium polyoxyethylene octyl phenyl ether sulfate; alkylamide sulfates such as sodium polyoxyethylene laurylamido ether sulfate, triethanolammonium polyoxyethylene laurylamido ether sulfate, sodium polyoxyethylene myristylamido ether sulfate, sodium polyoxyethylene oleylamido ether sulfate, sodium polyoxyethylene coconut oil fatty acid amide ether sulfate, and sodium oleylamido ether sulfate; acyl ester sulfates such as sodium hydrogenated coconut oil fatty acid glycerin sulfate; alkyl sulfonates such as sodium lauryl sulfonate, sodium myristyl sulfonate, and sodium coconut oil alkyl sulfonate; alkyl benzene sulfonates such as sodium linear dodecylbenzenesulfonate and triethanolammonium linear dodecylbenzenesulfonate; alkyl naphthalene sulfonate; formalin-condensed sulfonates such as formaldehyde polycondensation of naphthalene sulfonate; sulfosuccinate salts such as disodium lauryl sulfosuccinate, sodium di-2-ethylhexyl sulfosuccinate, disodium lauryl polyoxyethylene sulfosuccinate, and disodium oleamido sulfosuccinate; α-olefin sulfonates such as sodium dodecene sulfonate, sodium tetradecene sulfonate, potassium dodecene sulfonate, and potassium tetradecene sulfonate; α-sulfo fatty acid ester salts such as α-sulfo lauric acid methyl ester, α-sulfo myristyl acid methyl ester, and α-sulfo lauric acid (EO) n methyl ester; N-acyl methyltaurine salts such as potassium coconut oil fatty acid acyl-N-methyl taurinate, sodium lauroyl-N-methyl taurinate, potassium lauroyl-N-methyl taurinate, triethanolamine lauroyl-N-methyl taurinate, sodium myristoyl-N-methyl taurinate, triethanolamine myristoyl-N-methyl taurinate, sodium coconut oil fatty acid acyl-N-methyl taurinate, and triethanolamine coconut oil fatty acid acyl-N-methyl taurinate; acyl isethionates such as sodium lauroyl isethionate, sodium myristoyl isethionate, and sodium coconut oil fatty acid acyl isethionate; alkyl ether phosphates such as sodium polyoxyethylene lauryl ether phosphate, sodium polyoxyethylene cetyl ether phosphate, potassium polyoxyethylene myristyl phosphate, sodium polyoxyethylene oleyl ether phosphate, and sodium dipolyoxyethylene oleyl ether phosphate; alkyl aryl ether phosphate; fatty acid amide ether phosphates such as sodium polyoxyethylene lauryl amide ether phosphate; alkyl phosphates such as sodium lauryl phosphate, sodium myristyl phosphate, sodium coconut oil fatty acid phosphate, potassium myristyl phosphate, triethanolammonium lauryl phosphate, and diethanolamine oleyl phosphate; and a mixture thereof.

Among these anionic surfactants used in combination with the organosiloxane derivative, fatty acid soap, acylmethyltaurine salt, or alkyl ether carboxylate salt is preferably used. In particular, the combination with fatty acid soap is preferred when the cleanser is used as a skin cleanser, and the combination with acylmethyltaurine salt is preferred when the cleanser is used as a hair cleanser.

The amount of the various anionic surfactants incorporated in the cleanser of the present invention is not particularly limited and is usually 0.1 to 10% by mass, preferably 0.1 to 5% by mass, more preferably 0.3 to 2% by mass, of the total amount of the composition. If the amount of the various anionic surfactants is too small, a good foaming property may not be achieved. If the amount of the various anionic surfactants is too large an amount, there may be problems in terms of skin irritation. In the cleanser of the present invention, an appropriate amount of surfactants other than the above-mentioned various anionic surfactants (such as a non-ionic surfactant, a cationic surfactant, and an amphoteric surfactant) can be incorporated.

The cleanser of the present invention can be formulated with, in addition to the essential components, other components usually used in the cosmetic or medical field, for example, oils, waxes, moisturizers (e.g., ethylene glycol, propylene glycol, 1,3-butylene glycol, glycerin, polyglycerin, sorbitol, polyethylene glycol, hyaluronic acid, chondroitin sulfate, and pyrrolidonecarboxylic acid salts), thickeners, gelling agents, water-soluble polymers (e.g., xanthan gum, carboxymethylcellulose and carboxyvinyl polymer, alkyl-modified carboxyvinyl polymer, and hyaluronic acid), oil-soluble polymers, amino acids (e.g., serine and arginine), drugs (e.g., vitamin C, vitamin C derivatives, 4-methoxy salicylic acid, and tranexamic acid), antioxidants (e.g., tocopherols, dibutylhydroxytoluene, butylhydroxyanisole, and gallic acid esters), antiseptic agents (e.g., ethylparaben and butylparaben), disinfectants (e.g., cetylpyridinium chloride, benzethonium chloride, dequalinium chloride, benzalkonium chloride, chlorhexidine gluconate, carbanilide, phenol, and halogenated salicylanilide), natural extracts such as crude drugs (e.g., *phellodendron* bark, goldthread, lithospermum root, *paeonia albiflora, swertia japonica*, birch, sage, loquat, carrot, aloe, *malva sylvestris* (mallow), iris, *vitis vinifera* (grape), *coix lacryma-jobi* (job's tears), *luffa cylindrica*, lily, saffron, *enidium officinale*, ginger, *hypericum* perforatum, *ononis spinosa, allium sativum* (gerlic), *capsicum frutescens, citrus unshiu* peel, *angelica acutiloba*, and sea alga), water-soluble reducing agents, pH adjusters, pigments, dyes, pearlescent agents, lame agents, organic/inorganic powders, and perfumes, as needed, within a qualitative/quantitative range that does not impair the effects of the present invention.

The use application of the cleanser of the present invention is not particularly limited, and it can be used in various cleansers, for example, skin cleansers such as soap bars, liquid soaps, face cleansing scrubs, face cleansing forms, makeup removers (cleansings), and body shampoos, and hair cleansers such as shampoos and two-in-one shampoos.

EXAMPLES

Hereinafter, the present invention will be described more specifically with reference to Examples. However, the present invention is not intended to be limited to them.

The structures and synthesis methods of organosiloxane derivatives (compounds 1 to 4 and comparative compounds 1 to 4) used in Examples and Comparative Examples are shown below. In this context, each compound was identified by $^1H, ^{13}C, ^{29}Si$-NMR (NMR apparatus: Fourier Transform Nuclear Magnetic Resonance Spectrometer JEOL JNM-EX400 (manufactured by JEOL Ltd.).

Compound 1

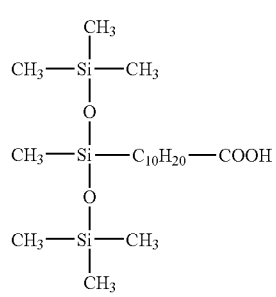

Synthesis Method of Compound 1

100 g of 1,1,1,3,5,5,5-heptamethyltrisiloxane and 0.02 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 100° C., 105 g of trimethylsilyl undecylenate was added dropwise to the flask. After the completion of the dropwise addition, the mixture was aged at 100° C. for 2 hours, and the completion of the reaction was then confirmed using gas chromatography. Low-boiling fractions were distilled off under reduced pressure. Then, methanol and water were added thereto, and the mixture was aged for 5 hours under reflux for deprotection. Then, low-boiling fractions were removed again under reduced pressure to obtain a compound 1. As a result of analysis, the compound 1 was confirmed to be represented by the chemical structural formula shown above.

Compound 2

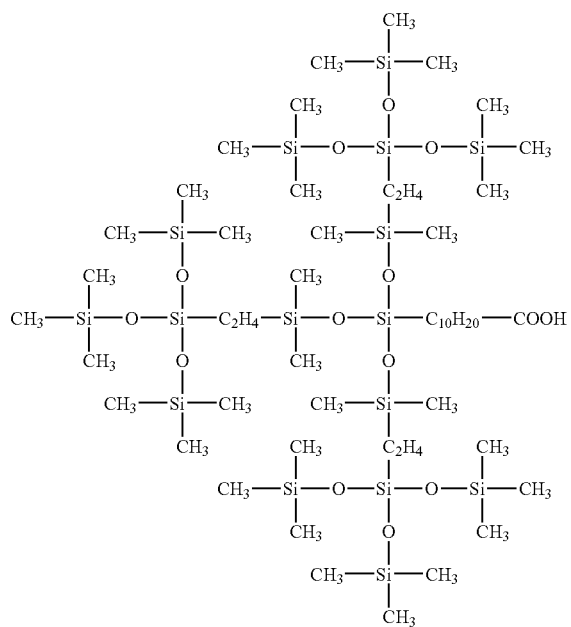

Synthesis Method of Compound 2

A flask equipped with a stirrer, a thermometer, a reflux condenser, and a dropping funnel was charged with 100 g of tetrakis(dimethylsiloxy)silane and 0.02 g of a toluene solution of a platinum-1,3-divinyl-1,1,3,3-tetramethyldisiloxane complex. The mixture was heated to 90° C. with stirring. Subsequently, while the reaction temperature was kept at 90° C., 15.6 g of trimethylsilyl undecylenate was gradually added dropwise thereto using the dropping funnel. After the completion of the dropwise addition, the reaction solution was heated at 100° C. for 1 hour. After cooling, the reaction solution was distilled under reduced pressure to obtain 35.3 g of a colorless, transparent liquid. As a result of analysis, this liquid was confirmed to be a compound represented by the structural formula shown below. This compound was designated as an intermediate 2A.

Intermediate 2A

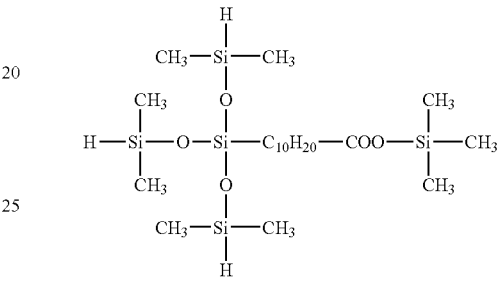

Next, 54.1 g of vinyl tris(trimethylsiloxy)silane and 0.01 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 100° C., 35 g of the intermediate 2A was added dropwise to the flask. After the completion of the dropwise addition, the mixture was aged at 100° C. for 2 hours. Then, the disappearance of the Si—H bonds was confirmed by FT-IR. Low-boiling fractions were distilled off under reduced pressure. Then, 8 g of methanol was added thereto, and the mixture was aged for 5 hours under reflux for deprotection. Then, low-boiling fractions were removed again under reduced pressure. As a result of analysis, the obtained compound was confirmed to be a compound 2 represented by the chemical structural formula shown above.

Compound 3

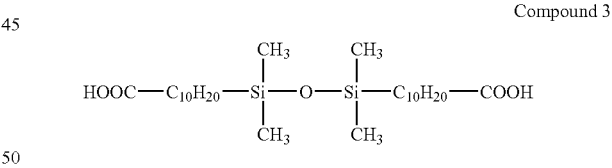

Synthesis Method of Compound 3

460.81 g of trimethylsilyl Undecylenate and 0.05 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 80° C., 100 g of 1,1,3,3-tetramethyldisiloxane was added dropwise to the flask. After the completion of the dropwise addition, the mixture was aged at 100° C. for 2 hours, and the completion of the reaction was then confirmed using gas chromatography. Low-boiling fractions were distilled off under reduced pressure. Then, 240 g of methanol was added thereto, and the mixture was aged for 5 hours under reflux for deprotection. Then, low-boiling fractions were removed again under reduced pressure to obtain a compound 3. As a result of analysis, the compound 3 was confirmed to be represented by the chemical structural formula shown above.

Compound 4

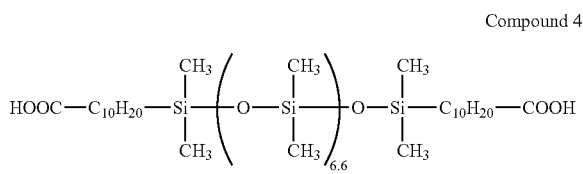

Synthesis Method of Compound 4

225.0 g of trimethylsilyl undecylenate and 0.05 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 80° C., 225 g of siloxane having Si—H at both ends, represented by the following formula was added dropwise to the flask.

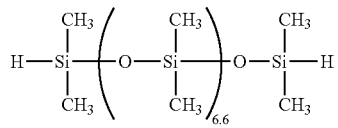

After the completion of the dropwise addition, the mixture was aged at 100° C. for 2 hours. Then, the disappearance of the Si—H bonds was confirmed by FT-IR. Low-boiling fractions were distilled off under reduced pressure. Then, 127 g of methanol was added thereto, and the mixture, was aged for 5 hours under reflux for deprotection. Then, low-boiling fractions were removed again under reduced pressure to obtain a compound 4. As a result of analysis, the compound 4 was confirmed to be represented by the chemical structural formula shown above.

Moreover, organosiloxane derivatives as comparative compounds 1 to 4 shown below were prepared according to the synthesis methods of the compounds 1 to 4.

Comparative compound 1

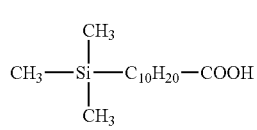

Comparative compound 2

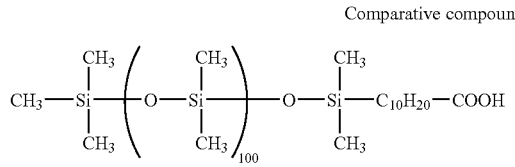

Comparative compound 3

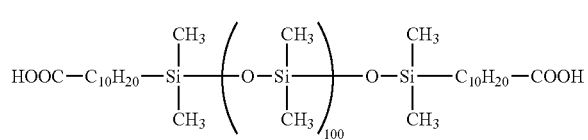

Comparative compound 4

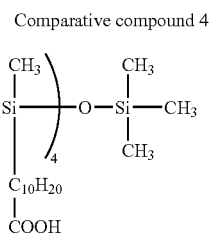

The present inventors studied the various organosiloxane derivatives thus prepared for the suitability as a cleansing component. Each composition shown in Tables 1 to 3 was prepared, and the usability in terms of foaming property, makeup cleansing capability, and hair wax cleansing capability was evaluated. The compositions and evaluation results used in the test are together shown in Tables 1 to 3 below. In this context, the detail of the test is as shown below.

Usage Test (Foaming Property, Makeup Cleansing Capability, and Hair Wax Cleansing Capability)

Cleansing was performed by ten professional panelists with use of each composition of the examples and the comparative examples, and the panelists conducted a sensory evaluation in terms of the foaming property, the makeup cleansing capability, and the hair wax cleansing capability according to a scoring system with five grades (1 to 5 points) as shown below. The evaluation of the property and capability of each composition was conducted according to the following criteria using the average of 10 panelists' scores calculated for each property and capability.

(Criteria)
◎: Very good (Average score is 4.5 points or higher)
O: Good (Average score is 3.5 points or higher and lower than 4.5 points)
Δ: Medial (Average score is 2.5 points or higher and lower than 3.5 points)
X: Bad (Average score is lower than 2.5 points)
Foaming Property
(Criteria of Scoring)
5 points: The composition is excellent in the foaming property (the volume of foam is large).
4 points: The composition is slightly excellent in the foaming property (the volume of foam is slightly large).
3 points: Medial
2 points: The composition is slightly poor in the forming property (the volume of foam is slightly small).
1 point: The composition is poor in the forming property (the volume of foam is small).
Makeup Cleansing Capability
(Criteria of Scoring)
5 points: The composition is excellent in the makeup cleansing capability.
4 points: The composition is slightly excellent in the makeup cleansing capability.
3 points: Medial
2 points: The composition is slightly poor in the makeup cleansing capability.
1 point: The composition is poor in the makeup cleansing capability.
Hair Wax Cleansing Capability
(Criteria of Scoring)
5 points: The composition is excellent in the hair wax cleansing capability.
4 points: The composition is slightly excellent in the hair wax cleansing capability.

3 points: Medial
2 points: The composition is slightly poor in the hair wax cleansing capability.
1 point: The composition is poor in the hair wax cleansing capability.

In the usage test, the following commercially available makeup cosmetics (foundation, lipstick, mascara) and hair wax were used. Any of these makeup cosmetics and hair wax contain a silicone compound.

Foundation: MAQUILLAGE Florence Skin Liquid UV (Shiseido Co., Ltd.)
Lipstick: MAQUILLAGE Color On Climax Rouge RD350 (Shiseido Co., Ltd.)
Mascara: MAQUILLAGE Mascara Combing Glamour (Shiseido Co., Ltd.)
Hair wax: UNO 2 Way Super Wax (Shiseido Co., Ltd.)

TABLE 1

|  | Example 1 | Example 2 | Example 3 | Example 4 | Comparative example 1 | Comparative example 2 |
|---|---|---|---|---|---|---|
| Sodium laurate | 30 | 30 | 30 | 30 | 30 | — |
| Compound 1 neutralized with sodium | 3 | — | — | — | — | 30 |
| Compound 1 neutralized with triethanolamine | — | 3 | — | — | — | — |
| Compound 2 neutralized with sodium | — | — | 3 | — | — | — |
| Compound 3 neutralized with sodium | — | — | — | 3 | — | — |
| Foaming property | ⊚ | ⊚ | ○ | ⊚ | ⊚ | X |
| Makeup cleansing capability | ⊚ | ⊚ | ⊚ | ○ | X | ⊚ |
| Hair wax cleansing capability | ⊚ | ⊚ | ⊚ | ○ | X | ⊚ |

TABLE 2

|  | Comparative Example 3 | Comparative Example 4 | Comparative Example 5 | Comparative Example 6 | Comparative Example 7 | Comparative Example 8 | Comparative Example 9 | Comparative Example 10 | Comparative Example 11 |
|---|---|---|---|---|---|---|---|---|---|
| Sodium laurate | 30 | 30 | 30 | 30 | 30 | 30 | 30 | 30 | 30 |
| Comparative compound 1 neutralized with sodium | 3 | — | — | — | — | — | — | — | — |
| Comparative compound 2 neutralized with sodium | — | 3 | — | — | — | — | — | — | — |
| Comparative compound 3 neutralized with sodium | — | — | 3 | — | — | — | — | — | — |
| Comparative compound 4 neutralized with sodium | — | — | — | 3 | — | — | — | — | — |
| Dimethicone | — | — | — | — | 3 | — | — | — | — |
| Silicone surfactant (HLB7.5) *1 | — | — | — | — | — | 3 | — | — | — |
| Silicone surfactant (HLB10) *2 | — | — | — | — | — | — | 3 | — | — |
| Liquid paraffin | — | — | — | — | — | — | — | 3 | — |
| Cetyl trioctanoate | — | — | — | — | — | — | — | — | 3 |
| Foaming property | ⊚ | X | X | X | X | X | Δ | X | X |
| Makeup cleansing capability | X | ○ | ⊚ | ⊚ | ○ | ○ | Δ | Δ | Δ |
| Hair wax cleansing capability | X | ○ | ⊚ | ⊚ | ○ | ○ | Δ | Δ | Δ |

*1: PEG/PPG-20/22 butyl ether dimethicone (KF6012: manufactured by Shin-Etsu Silicone)
*2: PEG 9 dimethicone (KF6013: manufactured by Shin-Etsu Silicone)

As shown in Table 1, in any of the cleansers of Examples 1 to 4 in which the organosiloxane derivative (any of compounds 1 to 3) and the fatty acid soap (sodium laurate) were incorporated, the effect of cleansing cosmetics (i.e., the makeup cleansing capability and the hair wax cleansing capability) was excellent, and the foaming property was also good. On the other hand, in Comparative Example 1 in which the fatty acid soap was used alone, the cleansing capabilities were poor though the foaming property was good. Also, Comparative Example 2, in which the organosiloxane derivative was used alone, could not achieve the foaming property at all though the cleansing effect was excellent.

In addition, as shown in Table 2, Comparative Example 3, in which the organosiloxane derivative with a short silicon group (comparative compound 1) was used, was poor in the cleansing capabilities, and any of Comparative Examples 4 to 6, in which the organosiloxane derivative with a long silicon group (any of comparative compounds 2 to 4) was used, could not achieve the foaming property at all owing to the antifoaming effect of the organosiloxane derivative, though the cleansing effect could be achieved. Also, in any of Comparative Examples 7 to 11 in which a silicone oil (dimethicone), the conventional silicone surfactant, a hydrocarbon oil (liquid paraffin), or an ester oil (cetyl trioctanoate) was used, a cleanser which was excellent in both of the foaming property and the cleansing effect could not be achieved.

TABLE 3

|  | Example 5 | Example 6 | Example 7 | Example 8 | Comparative Example 12 | Comparative Example 13 |
|---|---|---|---|---|---|---|
| Compound 1 | 0.5 | 3 | 10 | 18 | — | 33 |
| Ethanol | 10 | 10 | 10 | 10 | 10 | 10 |
| Glycerin | 10 | 10 | 10 | 10 | 10 | 10 |
| Diglycerin | 3 | 3 | 3 | 3 | 3 | 3 |
| Solbitol solution | 8 | 8 | 8 | 8 | 8 | 8 |
| Isostearic acid | 2 | 2 | 2 | 2 | 2 | — |
| Stearic acid | 5 | 5 | 5 | 5 | 5 | — |
| Myristic acid | 17.5 | 15 | 8 | 0 | 18 | — |
| Palmitic acid | 3 | 3 | 3 | 3 | 3 | — |
| Polyoxyethylene (25) polyoxypropylene (30) glycol | 3 | 3 | 3 | 3 | 3 | — |
| Coco amidopropyl betaine | 2 | 2 | 2 | 2 | 2 | — |
| Sodium hydroxide solution (48%) | 7 | 7 | 7 | 7 | 7 | 7 |
| Potassium hydroxide solution (47%) | 3 | 3 | 3 | 3 | 3 | 3 |
| Sucrose | 10 | 10 | 10 | 10 | 10 | 10 |
| Purified water | 16 | 16 | 16 | 16 | 16 | 16 |
| Foaming property | ◎ | ◎ | ○ | ○ | ◎ | X |
| Makeup cleansing capability | ○ | ○ | ◎ | ◎ | X | ◎ |

As is clear from Table 3, any of Examples 5 to 8, in which 0.5 to 18% by mass of the organosiloxane derivative of the present invention (compound 1) and the fatty acid soap were incorporated, were excellent in both of the cleansing effect and the foaming property. To the contrary, Comparative Example 12 which did not contain the organosiloxane derivative and Comparative Example 13 which did not contain the fatty acid were significantly poor in either the foaming property or the cleansing effect.

Hereinafter, formulation examples of the cleanser formulated with, the organosiloxane derivative of the present invention and the various anionic surfactants will be shown specifically. However, the present invention is not intended to be limited to them.

Formulation Example 1

Makeup Cleansing Soap

| (Components) | (mass %) |
|---|---|
| (1) Compound 1 | 2 |
| (2) Ethanol | 10 |
| (3) Glycerin | 10 |
| (4) Diglycerin | 3 |
| (5) Solbitol solution | 8 |
| (6) Isostearic acid | 2 |
| (7) Stearic acid | 5 |
| (8) Myristic acid | 15 |
| (9) Palmitic acid | 3 |
| (10) Polyoxyethylene (25) polyoxypropylene glycol (30) | 3 |
| (11) Sodium coconut fatty acid methyl taurinate | 0.1 |
| (12) 2-Alkyl-N-carboxymethyl-N-hydroxyethyl imidazolinium betaine | 2 |
| (13) Coco amidopropyl betaine | 2 |
| (14) Polychlorodimethylmethylene piperidinium | 0.5 |

-continued

| (Components) | (mass %) |
|---|---|
| (15) Titanium oxide | 0.1 |
| (16) Sodium hydroxide solution (48%) | 7 |
| (17) Potassium hydroxide solution (47%) | 3 |
| (18) Sodium chloride | 0.1 |
| (19) Sodium metaphosphate | 0.1 |
| (20) Dipotassium glycyrrhizinate | 0.05 |
| (21) Tetrasodium hydroxyethane diphosphonate (30%) | q.s. |
| (22) Trisodium hydroxyethyl ethylenediamine triacetate | q.s. |
| (23) Sucrose | 10 |
| (24) Purified water | balance |

(Production Method)

Into (24), (10) to (14) and (18) to (23) were added and dissolved therein. To the mixture, (1) to (9) were added and dissolved therein at 75° C., and then (16) and (17) were added thereto to neutralize the mixture. The obtained mixture was filled in a container and cooled to obtain a soap bar.

Formulation Example 2

Makeup Cleansing Soap

| (Components) | (mass %) |
|---|---|
| (1) Compound 2 | 4 |
| (2) Ethanol | 15 |
| (3) Solbitol solution | 10 |
| (4) Polyoxypropylene (9) diglyceryl ether | 4 |
| (5) Castor oil | 2 |
| (6) Isostearic acid | 2 |
| (7) Stearic acid | 7 |
| (8) Lauric acid | 6 |
| (9) Myristic acid | 11 |
| (10) Palmitic acid | 3 |
| (11) Sodium dodecan-1,2-diol acetate | 3 |
| (12) Sodium N-methyl taurine | 5 |
| (13) Sodium hydroxide | 4 |
| (14) Sodium chloride | 0.5 |
| (15) *Chamomilla recutita* extract | 0.1 |
| (16) Dibutylhydroxytoluene | q.s. |
| (17) Tetrasodium hydroxyethane diphosphonate (30%) | 0.1 |
| (18) Trisodium edetate | 0.1 |
| (19) 4-tert-butyl-4'-methoxybenzoylmethane | 0.05 |
| (20) 2-Ethylhexyl p-methoxycinnamate | 0.05 |
| (21) Mixture of sucrose and sorbit | 15 |
| (22) Pigment | q.s. |
| (23) Purified water | balance |
| (24) Perfume | q.s. |

(Production Method)

All of (1) to (12) and (14) to (23) were added and dissolved at 75° C., After the dissolution, the mixture was neutralized with (13), and then (24) was added thereto. The obtained mixture was quickly cooled to 25° C. to obtain the product.

Formulation Example 3

Makeup Cleansing Foam

| (Components) | (mass %) |
|---|---|
| (1) Compound 3 | 3 |
| (2) Glycerin | 6 |
| (3) Dipropylene glycol | 4 |
| (4) Isostearic acid | 2 |
| (5) Lauric acid | 8 |
| (6) Myristic acid | 5 |
| (7) Polyethylene glycol diisostearate | 4 |
| (8) Coconut oil fatty acid diethanolamide | 2.5 |
| (9) Triethanolammmonium coconut oil fatty acid sarcosinate | 10 |
| (10) 2-Alkyl-N-carboxymethyl-N-hydroxyethyl imidazolinium betaine | 13 |
| (11) Polychlorodimethylmethylene piperidinium solution | 0.5 |
| (12) Triethanolamine | 12.4 |
| (13) Sodium chloride | 0.5 |
| (14) Dibutyl hydroxytoluene | q.s. |
| (15) Trisodium edetate | q.s. |
| (16) Purified water | balance |
| (17) Perfume | q.s. |

(Production Method)

All of (1) to (11) and (13) to (16) were added and dissolved at 75° C. After the dissolution, the mixture was neutralized with (12), and then (17) was added thereto. The obtained mixture was quickly cooled to 25° C. to obtain the product.

Formulation Example 4

Makeup Cleansing Foam

| (Components) | (mass %) |
|---|---|
| (1) Compound 4 | 3 |
| (2) Glycerin | 25 |
| (3) Solbitol solution (70%) | 5 |
| (4) Polyethylene glycol 1500 | 10 |
| (5) White Beeswax | 1 |
| (6) Stearic acid | 9 |
| (7) Lauric acid | 4 |
| (8) Myristic acid | 10 |
| (9) Polyoxyethylene (25) polyoxypropylene glycol (30) | 2 |
| (10) Polyoxyethylene glyceryl isostearate | 2 |
| (11) Glyceryl monostearate (self emulsifying) | 2 |
| (12) Sodium coconut fatty acid methyl taurinate | 1.5 |
| (13) Lauryldimethylaminoacetic acid betaine | 1 |
| (14) Talc | 0.1 |
| (15) Potassium hydroxide | 4 |
| (16) *Paeonia suffruticosa* root extract | 0.1 |
| (17) *Melissa officinalis* (balm mint) leaf extract | 0.1 |
| (18) Trisodium edetate | q.s. |
| (19) Ethyl cellulose | q.s. |
| (20) Polyethylene powder | 3 |
| (21) Purified water | balance |
| (22) Perfume | q.s. |

(Production Method)

All of (1) to (14) and (16) to (21) were added and dissolved at 75° C. After the dissolution, the mixture was neutralized with (15), and then (22) was added thereto. The obtained mixture was quickly cooled to 25° C. to obtain the product.

Formulation Example 5

Hair Wax Cleansing Shampoo

| (Components) | (mass %) |
|---|---|
| (1) Compound 1 sodium salt | 3 |
| (2) Glycerin | 3 |
| (3) Polyoxyethylene lauryl ether (12EO) | 1 |
| (4) Coconut oil fatty acid diethanolamide | 3 |
| (5) Sodium coconut fatty acid methyl taurinate | 15 |
| (6) Lauryldimethylaminoacetic acid betaine | 4 |
| (7) Polymer JR-400 (manufactured by Amerchol corporation) | 0.6 |
| (8) Citric acid | 0.25 |
| (9) Anhydrous sodium hydrogen phosphate | 0.1 |
| (10) *Iris florentina* root extract | 0.02 |
| (11) Sodium benzoate | q.s. |
| (12) Disodium edetate | q.s. |
| (13) Water | balance |
| (14) Perfume | q.s. |

(Production Method)

All of (1) to (6) and (8) to (13) were added and dissolved at 60° C. After the dissolution, (7) was added to the mixture and stirred sufficiently. Then, (14) was added to the obtained mixture and quickly cooled to 25° C. to obtain the product.

Formulation Example 6

Hair Wax Cleansing Shampoo

| (Components) | (mass %) |
|---|---|
| (1) Compound 2 sodium salt | 3 |
| (2) Ethylene glycol distearate | 1.5 |
| (3) Coconut oil fatty acid ethanolamide | 5.5 |
| (4) Sodium coconut fatty acid methyl taurinate | 8 |
| (5) Coco amidopropyl betaine | 5 |
| (6) Polymer JR-400 (manufactured by Amerchol corporation) | 0.5 |
| (7) Citric acid | 0.5 |
| (8) Sodium chloride | 1.2 |
| (9) *Eriobotrya japonica* leaf extract | 0.1 |
| (10) Phenoxyethanol | 0.1 |
| (11) Sodium benzoate | q.s. |
| (12) Disodium edetate | q.s. |
| (13) Water | balance |
| (14) Perfume | q.s. |

(Production Method)

All of (1) to (5) and (7) to (13) were added and dissolved at 60° C. After the dissolution, (6) was added to the mixture and stirred sufficiently. Then, (14) was added to the obtained mixture and quickly cooled to 25° C. to obtain the product.

What is claimed is:

1. A cleanser comprising:
an organosiloxane derivative salt represented by following formula (1) or (3) and
one or more anionic surfactants selected from the group consisting of carboxylate salt with an alkyl group having 10 to 20 carbon atoms, sulfate salt with an alkyl group having 10 to 20 carbon atoms, sulfonate salt with an alkyl group having 10 to 20 carbon atoms, and phosphate salt with an alkyl group having 10 to 20 carbon atoms;

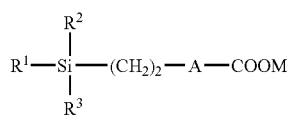

(1)

wherein in formula (1), at least one of $R^1$ to $R^3$ is a functional group represented by —O—Si($R^4$)$_3$ in which $R^4$ is an alkyl group having 1 to 6 carbon atoms or a phenyl group, or a functional group represented by —O—Si($R^5$)$_2$—$X^1$ in which $R^5$ is an alkyl group having 1 to 6 carbon atoms or a phenyl group, and $X^1$ is a functional group represented by following formula (2) when i=1; and remaining $R^1$ to $R^3$ may be the same or different and each may be a substituted or unsubstituted monovalent hydrocarbon group; M is a metal atom or an organic cation; A is a linear or branched alkylene group represented by $C_qH_{2q}$ in which q is any integer of 0 to 20; and the organosiloxane derivative represented by the formula (1) contains a total of 2 to 100 silicon atoms (Si) on average per molecule;

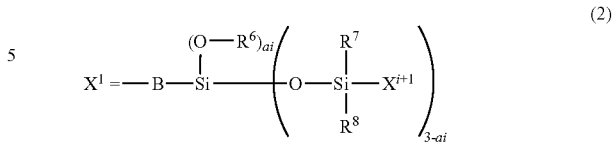

wherein in the formula (2), $R^6$ is a hydrogen atom, an alkyl group having 1 to 6 carbon atoms, or a phenyl group; $R^7$ and $R^8$ are respectively an alkyl group having 1 to 6 carbon atoms or a phenyl group; B is a linear or branched alkylene group represented by $C_rH_{2r}$ which may be partially branched in which r is any integer of 2 to 20; and i specifies generation of a silylalkyl group represented by $X^i$ and is any integer of 1 to n when the generation number is n, wherein the generation number n is any integer of 1 to 10; ai is any integer of 0 to 2 when i is 1, and is an integer smaller than 3 when i is 2 or larger; and $X^{i+1}$ is silylalkyl group when i is smaller than n, and is a methyl group when i=n.

2. The cleanser according to claim 1, wherein the organosiloxane derivative salt is represented by the formula (1), and $R^1$ and $R^2$ are respectively a functional group represented by —O—Si($R^4$)$_3$ in which $R^4$ is an alkyl group having 1 to 6 carbon atoms; $R^3$ is a monovalent hydrocarbon group having 1 to 10 carbon atoms; and q is any integer of 6 to 20.

3. The cleanser according to claim 1, wherein the organosiloxane derivative salt is represented by the formula (1), and at least one or more of $R^1$ to $R^3$ are respectively a functional group represented by following formula (4) or (5), and remaining $R^1$ to $R^3$ may be the same or different and are respectively a substituted or unsubstituted monovalent hydrocarbon group

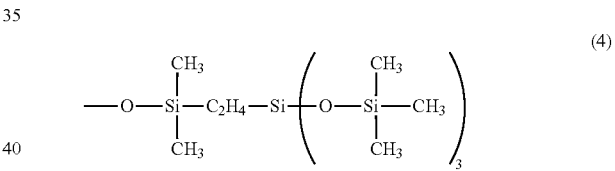

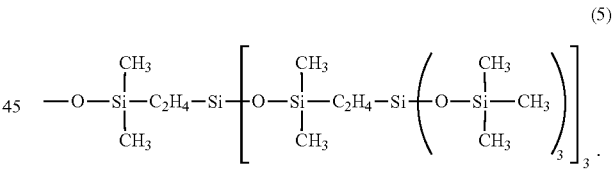

4. The cleanser according to claim 1, wherein the anionic surfactant is at least one selected from the group consisting of fatty acid soap, acylmethyltaurine salt, and alkyl ether carboxylic acid salt.

5. The cleanser according to claim 2, wherein the anionic surfactant is at least one selected from the group consisting of fatty acid soap, acylmethyltaurine salt, and alkyl ether carboxylic acid salt.

6. The cleanser according to claim 3, wherein the anionic surfactant is at least one selected from the group consisting of fatty acid soap, acylmethyltaurine salt, and alkyl ether carboxylic acid salt.

7. The cleanser according to claim 1, wherein the organosiloxane derivative represented by the formula (1) contains a total of 2 to 30 silicon atoms (Si) on average per molecule.

8. The cleanser according to claim 1, wherein the organosiloxane derivative represented by the formula (1) contains a total of 2 to 16 silicon atoms (Si) on average per molecule.

* * * * *